US008206396B2

(12) United States Patent
Trabish

(10) Patent No.: US 8,206,396 B2
(45) Date of Patent: Jun. 26, 2012

(54) FEMORAL HEAD SURGICAL RESURFACING AID

(76) Inventor: Harutaro Trabish, Folsom, CA (US)

( * ) Notice: Subject to any disclaimer, the term of this patent is extended or adjusted under 35 U.S.C. 154(b) by 310 days.

(21) Appl. No.: 12/497,324

(22) Filed: Jul. 2, 2009

(65) Prior Publication Data

US 2010/0016986 A1 Jan. 21, 2010

Related U.S. Application Data

(60) Provisional application No. 61/082,227, filed on Jul. 21, 2008.

(51) Int. Cl.
*A61B 17/56* (2006.01)
(52) U.S. Cl. .......................................... 606/89; 606/86 R
(58) Field of Classification Search ............... 606/79, 606/81, 84, 86, 89, 96, 98, 151, 166, 53, 606/80, 86 R; 623/10; 269/249
See application file for complete search history.

(56) References Cited

U.S. PATENT DOCUMENTS

| 3,099,441 | A | * | 7/1963 | Ries ................................. 5/637 |
| 3,945,377 | A | * | 3/1976 | Kronner ........................ 606/96 |
| 4,896,663 | A | * | 1/1990 | Vandewalls .................... 606/79 |
| 5,766,221 | A | * | 6/1998 | Benderev et al. .............. 606/96 |
| 5,891,150 | A | * | 4/1999 | Chan .............................. 606/98 |
| 5,976,149 | A | | 11/1999 | Masini |
| 6,743,235 | B2 | | 6/2004 | Subba Rao |
| 7,273,499 | B2 | | 9/2007 | McCleary et al. |
| 2005/0148843 | A1 | | 7/2005 | Roose |
| 2005/0245934 | A1 | | 11/2005 | Tuke et al. |
| 2006/0058886 | A1 | | 3/2006 | Wozencroft |
| 2008/0287954 | A1 | | 11/2008 | Kunz et al. |

* cited by examiner

*Primary Examiner* — Brian E. Pellegrino
(74) *Attorney, Agent, or Firm* — Patrick J. S. Inouye

(57) ABSTRACT

A femoral head surgical resurfacing aid that includes a C-shaped band with an interior surface conformed to fit a femoral neck of a patient is presented. An arch extends from one side of the C-shaped band to the other side of the C-shaped band and further extends over a femoral head of the patient. An alignment tube guide is positioned along the arch and extends outward from the arch.

7 Claims, 4 Drawing Sheets

FEMORAL HEAD SURGICAL RESURFACING AID

CROSS-REFERENCE

This nonprovisional patent application claims priority under 35 USC §119(e) to U.S. provisional patent application, entitled "Custom Self Clamping Hip Resurfacing Surgical Aid," Ser. No. 61/082,227, filed Jul. 21, 2008, the disclosure of which is incorporated by reference.

FIELD

The present invention relates in general to hip resurfacing surgical aids and, in particular, to a femoral head surgical resurfacing aid.

BACKGROUND

Joint cartilage is fibrous connective tissue providing cushioning between bones. Disease and physical disorders, such as osteoarthritis, rheumatoid arthritis, and avascular necrosis; benign or malignant bone tumors; excessive physical activity; and hereditary defects can cause cartilage tearing, erosion, or degeneration. Osteoarthritis, for instance, can occur following trauma to a joint region, or due to genetic predisposition or obesity. The disease is characterized by a premature wearing down or "erosion" of the cartilage surrounding a joint between two bones. The wear can lead to the bones rubbing directly against one another, which in turn causes pitting and malformation of the bone surfaces accompanied by pain and encumbrance of range of motion. Osteoarthritis treatment regimens include resting the affected joint, prescription of pain relief and anti-inflammatory medication, improved diet, and low impact exercise. In severe cases, surgical intervention, such as arthroplasty surgical procedures, may be necessary to repair the damaged or dysfunctional joint surfaces.

Hip joints are particularly susceptible to cartilage compromise and hip arthroplasty, commonly called "total hip replacement" (THR), attempts to relieve the pain associated with, and to restore the integrity and functionality of, damaged hip joints. In THR, the upper portion of the femur, including the femoral head and neck, is removed to receive the stem portion of a prosthetic implant. While generally successful, further post-THR hip joint deterioration may necessitate revision surgery, which entails radical femur restructuring by splitting apart the femur to remove the THR prosthesis stem and surgically rebuilding the femur, a more costly and involved procedure with extended convalescence.

Recently, hip resurfacing has emerged as a viable surgical alternative to THR, which is especially suitable for younger and more active patients. Hip resurfacing entails implantation of a hip joint prosthesis, generally formed of a femoral head prosthesis and an acetabular prosthesis. Unlike THR, the upper portion of the femur is retained intact and the femoral head is, instead reshaped to accept a less extensive prosthetic femoral cap. Resurfacing requires less bone removal, which can result in easier revision surgery, if later needed, by preserving more bone stock.

Precise alignment of the femoral head prosthesis along the central access of the femoral neck and of the acetabular prosthesis to the acetabulum is essential to successful hip resurfacing. Any misalignment can result in pain and affect the degree of leg extension and joint rotation. Typically, X-rays, computed tomography (CT) scans, magnetic resonance imaging (MRI), or other forms of nor-invasive imaging are taken of the hip joint and surrounding bony structures for planning the hip resurfacing procedure. Surgical templates are used along with the images to approximate the size and implantation axis of the prosthesis.

The preoperatively planned positions of the femoral head prosthesis and acetabular prosthesis must be transferred to the actual patient in the surgical theater, which is a manual and inherently imprecise process. During conventional hip resurfacing surgery, a pilot hole is drilled through the center of the femoral head along the planned axis of the femoral head prosthesis and a guide rod is inserted for a reaming device to follow during resurfacing. Determining the position and axis of the pilot hole during surgery, even with preoperative planning, is a manual, lengthy, and potentially error prone procedure, highly dependent upon the skill of the surgeon, quality of imaging, and patient condition.

Conventionally, an alignment guide, or jig, is used to orient and place the guide rod into the femoral head in a position that is in line with the central axis of the femoral neck. For instance, U.S. Patent Pub. No. 2005/0245934, filed Apr. 20, 2005, to Tuke et al., discloses an alignment guide for use in femoral head resurfacing surgery. The guide is placed around the neck of the femur and an alignment rod is manipulated into position over the femoral head. The rod is lowered onto the femoral head and locked into position. A drill is inserted through the rod to drill a pilot hole in the femoral head for later use in reaming device alignment. With practice, an acceptable pilot hole can be drilled, yet correct placement requires frequent manual readjustments of the guide to maintain proper positioning of the rod throughout the procedure.

SUMMARY

An embodiment provides a femoral head surgical resurfacing aid that includes a C-shaped band with an interior surface conformed to fit a femoral neck of a patient. An arch extends from one side of the C-shaped band to the other side of the C-shaped band and further extends over a femoral head of the patient. An alignment tube guide is positioned along the arch and extends outward from the arch.

A further embodiment provides a method for aligning a femoral head prosthesis implant axis. A femoral head surgical resurfacing aid is provided and includes a C-shaped band with an interior surface conformed to fit a femoral neck of a patient. An arch extends from one side of the C-shaped band to the other side of the C-shaped band and further extends over a femoral head of the patient. An alignment tube guide is positioned along the arch and extends outward from the arch. The axis of the alignment tube guide is parallel and in-line with a planned femoral head prosthesis implant axis. The femoral head surgical resurfacing aid is placed in position on the femoral neck of the patient. A boring tool is inserted through the alignment tube guide and a pilot hole is drilled into the femoral head with the boring tool.

Still other embodiments will become readily apparent to those skilled in the art from the following detailed description, wherein are described embodiments by way of illustrating the best mode contemplated. As will be realized, other and different embodiments are possible and their several details are capable of modifications in various obvious respects, all without departing from the spirit and the scope. Accordingly, the drawings and detailed description are to be regarded as illustrative in nature and not as restrictive.

DETAILED DESCRIPTION

Figure 1:
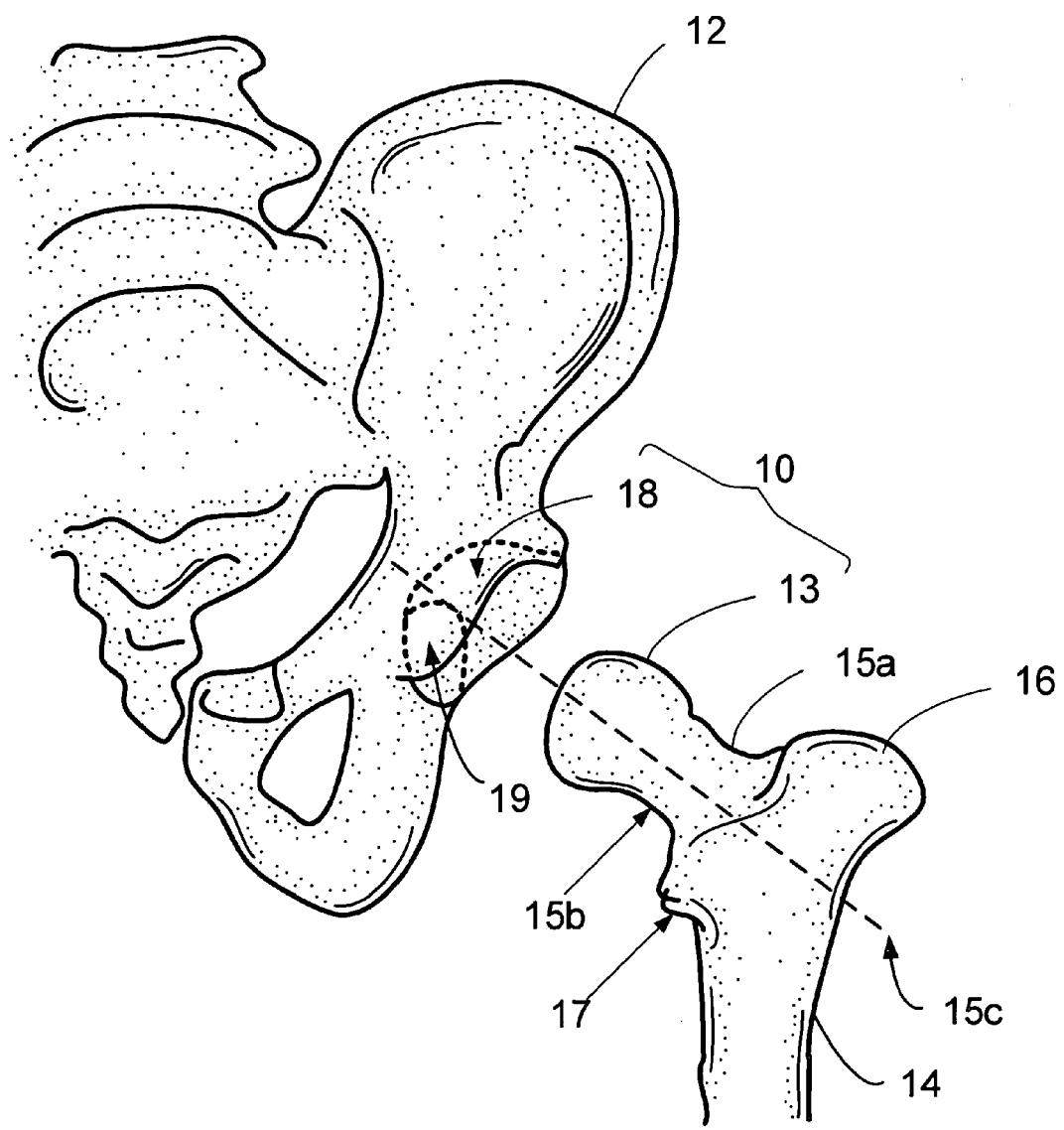
FIG. 1 is a side view showing, by way of example, a hip joint with the femur dislocated from the pelvis for clarity.

The hip joint is key to providing both mobility during walking and running and to ensuring stability during standing and other weight-bearing activities. The hip joint provides an important shock absorption function to the upper body due to impact from walking. As way of background, FIG. 1 is a side view showing, by way of example, a hip joint 10 with the femur 11 dislocated from the pelvis 12 for clarity. A femoral head 13 forms a ball at the proximal end of the femoral body 14 separated by a femoral neck 15a that meets the femoral head 13 at the femoral head-neck junction 15b. Greater trochanter 16 and lesser trochanter 17 bony prominences abutting the femoral body 14 form a base from which the femoral neck 15a extends. In a healthy patient, cartilage covers the femoral head 13 and provides cushioning between the femoral head 13 and pelvis 12.

The femoral head 13 articulates within the pelvis 12 at the acetabulum 18 to form the hip joint 10. The acetabulum 18 forms a cup-shaped depression on either side of the pelvis 12 to receive the femoral head 13. The acetabular fossa 19 is an indented region located at the bottom of the cavity of the acetabulum 17. Implantation of a femoral head prosthesis, as further described infra, and alignment of a reaming device for resurfacing of the femoral bead 13 in preparation for the prosthesis, is ideally along the central axis 15c of the femoral neck 15a.

Figure 2:
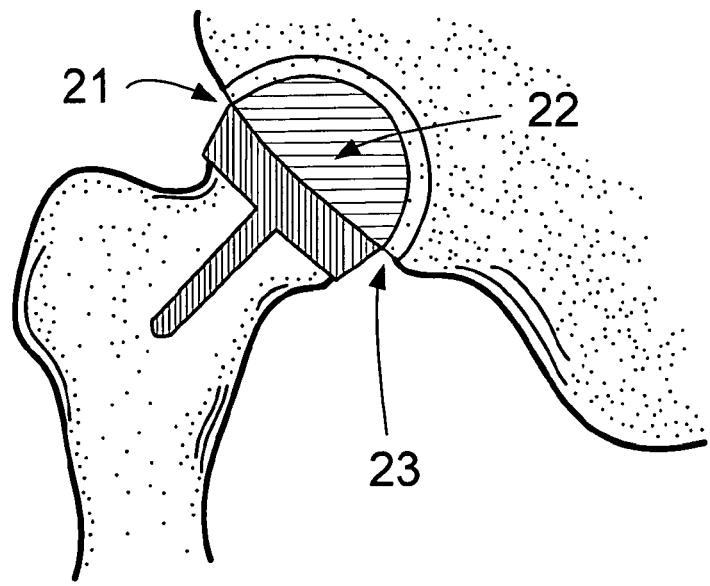
FIG. 2 is a side view showing a prior art resurfaced hip joint.

During hip resurfacing surgery, hip joint cartilage is removed and a hip joint prosthesis 21 implanted to replace the natural hip joint 10. FIG. 2 is a side view showing a prior art resurfaced hip joint 20. A full hip joint prosthesis 21 has two parts: a femoral head prosthesis 22 and an acetabular prosthesis 23, which respectively replace the functionality of the femoral head 13 and acetabulum 17. The femoral head prosthesis 22 is implanted into the resurfaced femoral head 13, while the acetabular prosthesis 23 is implanted in the acetabulum 17.

Conventionally, surgeons rely on non-invasive imaging, for example, X-ray, CT scan, and MRI, to determine the approximate sizes and alignments of the femoral head prosthesis 22 and acetabular prosthesis 23. In surgery, the femoral head 13 is dislocated and the approximated size of the femoral head prosthesis 23 is confirmed in situ by placing a surgical head template around the femoral neck 15a.

Accurate determination of the position on the femoral head 13 relative to the central axis of the femoral neck 15a is critical to the correct positioning of the guide wire, the various cutters, reamers, and reshaper tools, aid the femoral head prosthesis 22 during surgery. Moreover, insufficient clearance for the femoral head prosthesis 22 can lead to notching of the femoral neck 15a during resurfacing by the reaming device and weakening of the post-surgical hip. A jig (not shown) is utilized to determine the point on the femoral head 13 that aligns with the central axis 15c of the femoral neck 15a. The jig is generally attached to or placed circumferentially on the femur 11. A guide mechanism on the jig can be adjusted through all dimensional planes to confirm the correct axis of alignment for the femoral head prosthesis 22. Once aligned, the guide mechanism can be locked into position on the jig and a guide wire is inserted into the femoral head 13 along the determined axis, after which the jig is disassembled and removed. A reaming device mounts to the guide wire and trims the femoral head 13 flush to the femoral neck 15a. The femoral head 13 can be trimmed further, as necessary, so that the mouth of the femoral head prosthesis 22 is at the level of the femoral head-neck junction 15b. Another reaming device cuts a chamfer, or beveled edge, on the femoral head 13. The guide wire is removed and the femoral head prosthesis 22 cemented into place.

Similarly, correct determination of the axis of placement of the acetabulum reaming device is necessary for correct placement of the acetabular prosthesis 23. Conventionally, the axis is manually approximated by the surgeon either during the reaming process or by positioning a guide near the acetabulum 18 at an angle approximating the planned axis. The acectabulum 18 is prepared for the acetabular prosthesis 23 by first removing cartilage and any osteophytes that may have formed. The acetabulum is then reduced to receive the acetabular prosthesis 23. The pre-operative axis of the acetabular prosthesis 23 is adjusted, as necessary, and impacted into position.

Figure 3:
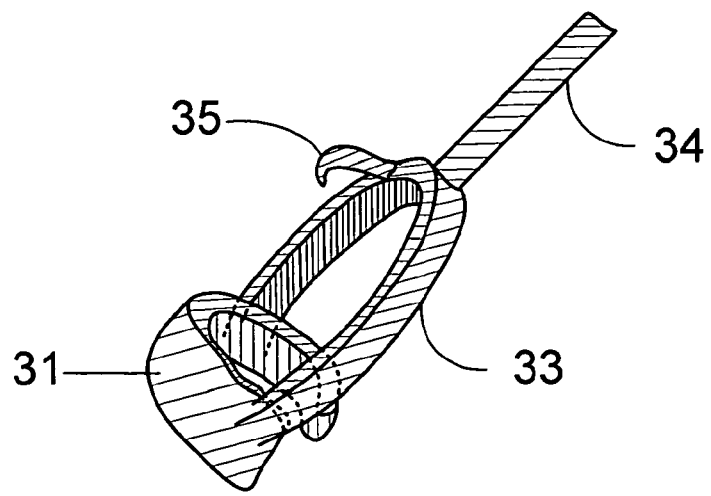
FIG. 3 is a perspective view showing a femoral head surgical resurfacing aid in accordance with one embodiment.

Rapid and precise placement of the femoral head prosthesis 22 along a pre-operatively planned implantation axis can be facilitated by replacing prior art hip resurfacing surgical alignment guides with femoral head surgical resurfacing aids that are custom-designed to patient specific features. FIG. 3 is a perspective view showing a femoral head surgical resurfacing aid 30 in accordance with one embodiment. The femoral head surgical resurfacing aid 30 enables efficient and fixed placement and ready removal of the aid 30. Each aid 30 is uniformly fabricated from a biocompatible, flexible material. Preferably, the material is well suited for rapid prototype manufacturing, as further described infra. Examples of such material include medical grade plastics, such as polycarbonate and acrylonitrile butadiene styrene (ABS). Other materials for construction of the femoral head surgical resurfacing aid 30 are possible.

The femoral head surgical resurfacing aid 30 includes a C-shaped band 31 that fits snugly and conformably around the femoral neck 15a, which inhibits movement or slippage. The opening 32 of the C-shaped band is slightly smaller than the femoral neck 15a, typically three millimeters to ten millimeters smaller. Other sizes are possible. An arch 33 is formed on opposite sides of the exterior of the C-shaped band 31 slightly back from the edges of the opening 32 and extends perpendicularly over the femoral head 13 when placed in situ, as discussed further below with reference to FIGS. 4 and 5. The arch 33 is typically five millimeters larger than the femoral head 13 and follows the contour of the head 13, though other sizes are possible. The dimensions of the arch 33 are generally ten millimeters by seven millimeters. Other dimensions are possible. The arch 33 is integrally constructed as part of the femoral head surgical resurfacing aid 30, as also discussed further infra.

An alignment tube 34 projects perpendicularly outward from the top of the arch 33 and extends axially away from the femoral head. The alignment tube 34 has an inner diameter sized to receive a boring tool, which is used to bore a pilot hole for guide wire placement, as discussed above with reference to FIG. 2. Typically, the pilot hole is three millimeters to four millimeters. The outer diameter of the alignment tube 34 is 10 millimeters, with a length of 45 millimeters from the outer surface of the C-shaped band 31. Other dimensions are possible.

The alignment tube 34 is oriented along the top of the arch 33 such that the axis of the alignment tube 34 is parallel to and in line with the pre-operative femoral head prosthesis axis.

The alignment tube 34 is preferably constructed such that the outer diameter of the tube 34 matches the width of the arch 33, which enables the alignment tube 34 to be easily removed, such as "snap off" by the arch 33. Removal of the alignment tube 34 also splits the arch in two lengthwise pieces, enabling rapid removal of the femoral head surgical resurfacing aid 30.

In a further embodiment, one or more stabilizers 35 extend from the sides of the arch 33 to contact the surface of the femoral head 13 in situ when the femoral head surgical resurfacing aid 30 is rotated into position. The femoral head surgical resurfacing aid 30 can include one or more stabilizers 35 depending upon the shape of the aid and the stability required. The stabilizers 35 can extend from either side and at any point along the arch 33. Each stabilizer 35 is claw-shaped with a rounded or pointed end that downturns distally to contact the femoral head 13 when placed in situ. Other stabilizer shapes are possible, such as spherical and cylindrical.

The stabilizers 35 counter any lateral tilting pressure, such as may be applied when a boring tool is inserted through the alignment tube 34. The stabilizers 35 thereby help prevent slippage and misalignment. Stabilizers 35 are uniformly and integrally fabricated with, and are constructed from the same material, as the rest of the aid 30, as discussed further infra. Additionally, the stabilizers 35 placement, length, and orientation are custom-designed based on patient-specific features of the femoral head 13, as discussed further below with reference to FIG. 4.

With the femoral head surgical resurfacing aid 30 placed around the femoral head 13 in situ, a boring tool can be used to bore a pilot hole. The dimensions of the pilot hole are generally dependent on the requirements of the manufacturer of the implant. Once the pilot hole is bored and the boring tool removed, the alignment tube 34 can be snapped off to facilitate efficient removal of the femoral head surgical resurfacing aid 30. Femoral head resurfacing then proceeds as discussed above with reference to FIG. 2.

Preferably, the femoral head surgical resurfacing aid 30 is rapid prototyped based on patient-specific physical femoral features. A patient's hip joint region is scanned using a no invasive imaging technique, such as CT or MRI. The imaging is imported into a computer aided design (CAD) program or other three-dimensional modeling software loaded into a computer system, for example, 3D-DOCTOR, available from Able Software Corporation, Lexington, Mass. The computer system is a general purpose, programmed digital computing device consisting of a central processing unit (CPU), random access memory (RAM), non volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage.

The CAD program segments the bone structures to create a three-dimensional model of the acetabulum 18 and the femur 11. The three-dimensional model is then used for preoperative planning of the size and implantation axis of the femoral head prosthesis 22 according to the anatomical structure of the patient. Additionally, key landmark points on the femur 11 are identified, including bony structures and protuberances, for example, the intertrochanteric crest that connects the greater trochanter 16 and lesser trochanter 17, and depressions, ridges, scars, and striations.

A three-dimensional model of the femoral head surgical resurfacing aid 30 is generated by the CAD program using the key landmark points, the patient-specific surface structure of the femur, and the planned position of the femoral head prosthesis 22. For example, the surface structure and key landmarks are used to render the dimensions and inside surface of the C-shaped band 31 to conformably follow the femoral neck 15a contours. Similarly, the planned axis of implantation of the femoral head prosthesis 22 is used to position the alignment tube 34 in-line with the implantation axis and to position the arch 33 along the C-shaped band 31 so that the arch 33 intersects the planned axis. Stabilizer 35 length and position along the arch 33 are based on the surface structure and identified key landmarks of the femoral head 13. For example, the curvature of the femoral head 13 can be used to determine the downward angle of the stabilizers 35, while patient-specific surface features, such as striations and scars, can be used as the points at which the stabilizers 35 contact the femoral head 13. The model of the femoral head surgical resurfacing aid 30 is stored in memory and is provided to or electronically transmitted over an intranetwork or internetwork, such as the Internet, to a rapid prototype system, such as the FDM 400mc, manufactured by Stratasys, Inc., Eden Prairie, Minn., to fabricate the aid 30.

In a further embodiment, an existing femoral head surgical resurfacing aid 30 model is digitally manipulated by morphing, stretching, and warping to create the patient-specific model based on the anatomical structures of the patient, the key landmark points, and the planned prosthesis position. The model can be viewed and adjusted as necessary prior to fabrication.

In a still further embodiment, patient information (not shown) can be printed, engraved or marked on the surface of the aid 30. Patient information can include patient name, patient identification number, name of surgeon, hospital name, identification of which hip joint is to be replaced, rotation direction of the aid 30, and the type and size of prosthesis to be used. Including patient information directly on the aid 30 can assist with routing the aid 30 to the proper patient or hospital and aid the surgeon while performing surgery, such as circumstances wherein a patient is undergoing total hip replacement on both hips simultaneously.

Figure 4:
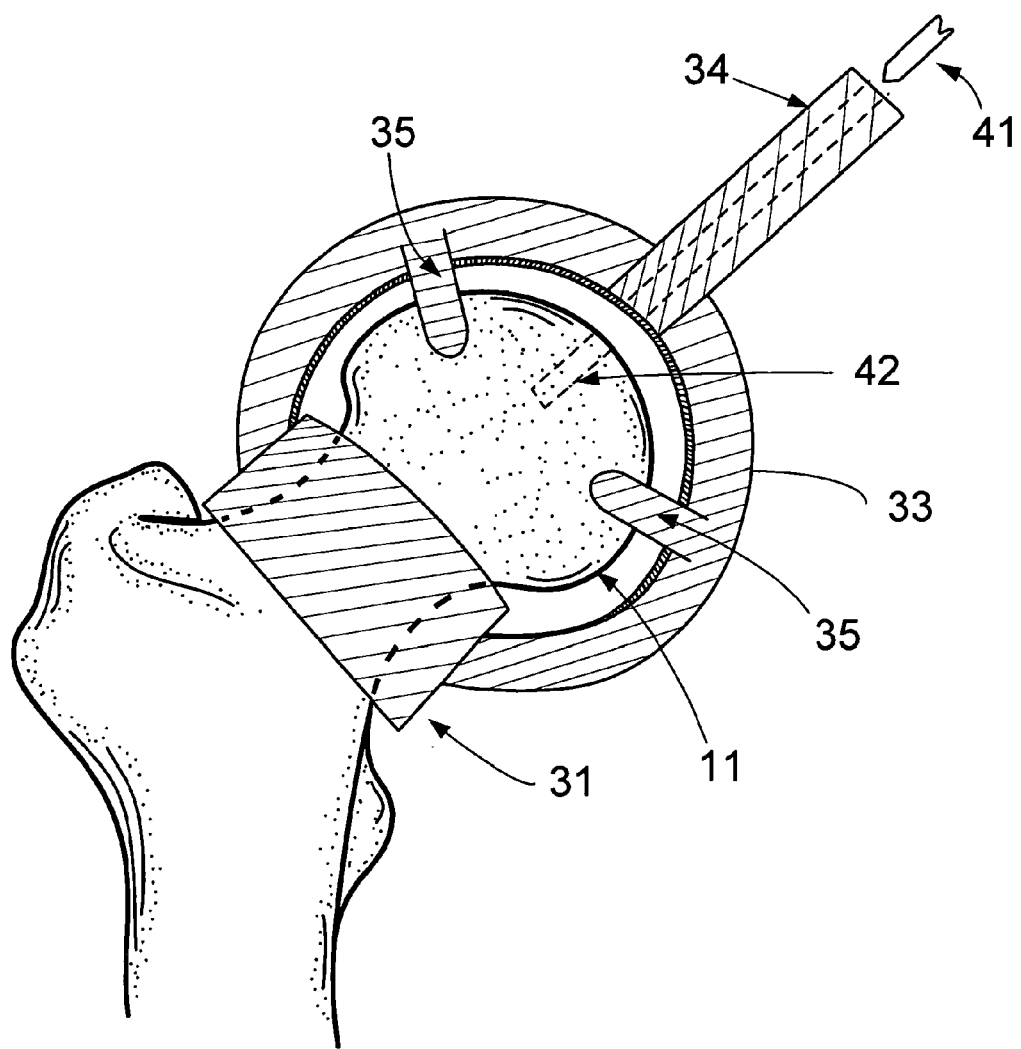
FIGS. 4 and 5 are opposite side views showing the femoral head surgical resurfacing aid in position on the femoral neck.
Figure 5:
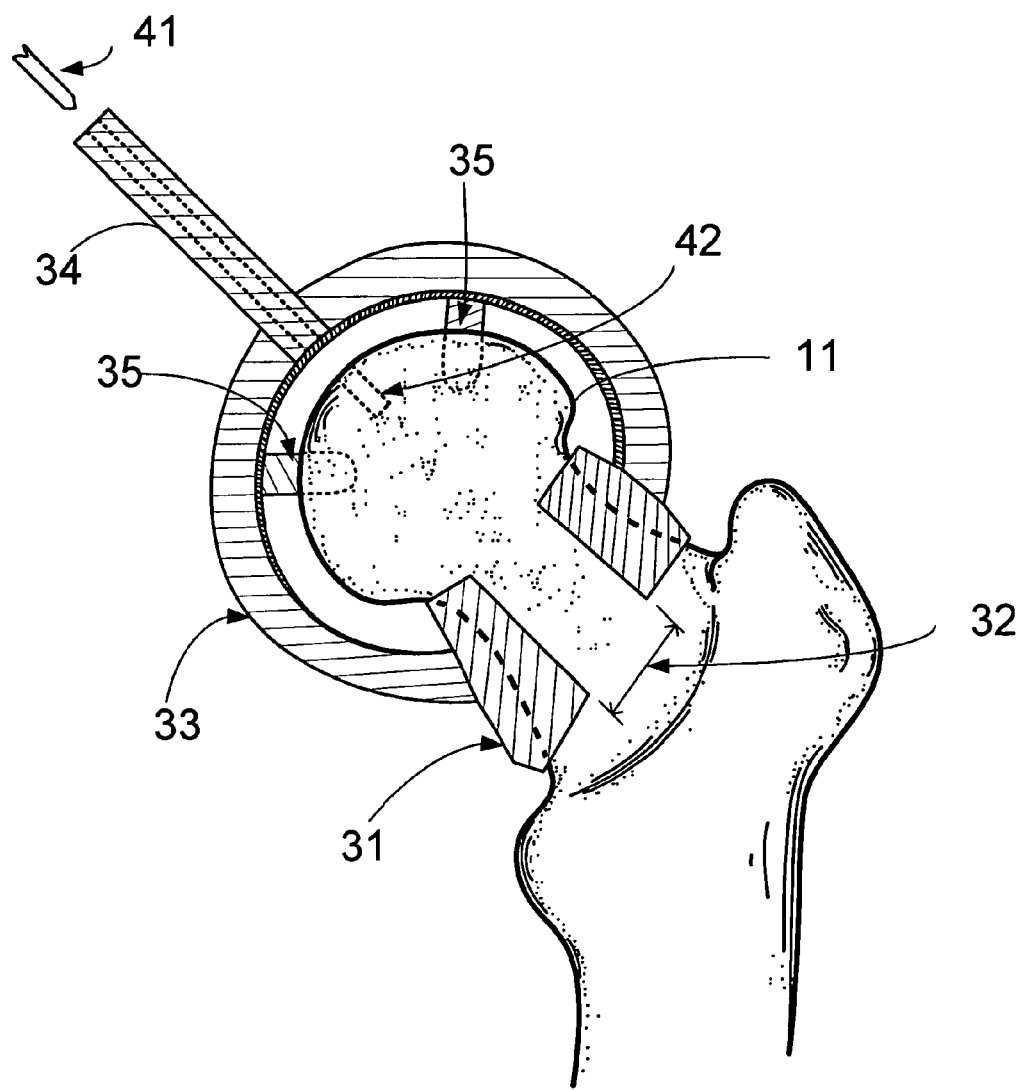

The femoral head surgical resurfacing aid 30 is used to accurately align the femoral head prosthesis 22 according to a pre-operative surgery plan. FIGS. 4 and 5 are opposite side views showing the femoral head surgical resurfacing aid 30 in position on the femoral neck 15a. The femoral head surgical resurfacing aid 30 can be placed on the femoral neck 15a from either the top or bottom of the femoral neck 15a and then rotated into position. The rotational direction, that is, clockwise or counterclockwise, can be printed, engraved, or marked on the surface of the aid (not shown).

The inside surface of the C-shaped band 31 conformably follows the surface of the femoral neck 15a when placed into position in situ. Matching the surface of the femoral neck 15a allows the C-shaped band 31 to automatically lock into place by virtue of the slightly elliptical shape of the femoral neck's cross section. Additionally, as the C-shaped band 31 spans both the femoral head-neck junction 15b and the greater trochanter-femoral neck junction 32, the femoral head surgical resurfacing aid 30 is securely fixed in place and prevented from slipping towards or away from the femoral head 13. Further, the flexible nature of the aid provides additional purchase during surgical manipulation.

In a further embodiment, the stabilizers 35 provide additional lateral support to the aid 30. One or more stabilizers 35 extend outwardly from the arch 33 and downward to touch the surface of the femoral head 13 when the femoral head surgical resurfacing aid 30 is placed in situ. The stabilizers 35 prevent movement of the aid 30 during boring of the pilot hole 42 into the femoral head 13. Patient-specific femoral head 13 surface features can be used to determine the position and length of the stabilizers 35, as discussed further above with reference to FIG. 3. For example, a claw-shaped stabilizer 35 can be positioned such that the distal end of the stabilizer 35 grips a striation on the surface of the femoral head 13.

As shown in FIG. 5, the C-shaped band 31 of the femoral head surgical resurfacing aid 30 has an opening 32 that allows the femoral head surgical resurfacing aid 30 to be slipped onto the femoral neck and frictionally fixed in place. The opening 32 is slightly smaller than the size of the femoral neck 15*a*, typically three millimeters to ten millimeters smaller. Since the femoral head surgical resurfacing aid 30 is constructed of a rigid, but flexible material, the femoral head surgical resurfacing aid 30 can be pushed over the femoral neck 15*a* and then rotated into position.

In a further embodiment, the femoral head surgical resurfacing aid 30 contains one or more fixed points (not shown) that can provide further confirmation the aid 30 is properly placed. Conventionally, a digitizer coupled to a navigation system is used to register, or map, points on the surface of bone to their corresponding position in a scanned image of the bone. Such feature-based registration can aid in correct positioning of implants during computer-assisted surgery. Similarly, the fixed points of the femoral head surgical resurfacing aid 30 can be used to register the position of the fixed points with positions in a scanned image of bone structures, such as discussed supra. The registration can then provide additional verification that the aid 30 is in the correct position on the femoral neck 15*a*. The fixed points can be added to the femoral head surgical resurfacing aid 30 as part of the three-dimensional model generation process, as discussed supra. In a further embodiment, the fixed points can be added post-fabrication. The fixed points can be depressions or holes in, or protrusions from, the outer surface of the aid 30. Other types of fixed points are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A femoral head surgical resurfacing aid, comprising:
   a C-shaped band constructed of flexible material and defining an elliptical shape with an interior surface slightly smaller than a femoral neck of a patient and conformed to follow the surface of the femoral neck, the C-shaped band further defining an opening configured to enable the C-shaped band to be slipped over the femoral neck and be frictionally fixed in place on the femoral neck upon rotation of the C-shaped band and engagement of the elliptical shape with the cross section of the femoral neck, wherein the width of the C-shaped band substantially spans the femoral head-femoral neck junction and the greater trochanter-femoral neck junction;
   an arch integrally constructed as part of the C-shaped band of the same flexible material and defining a shape following the contour of the femoral head, wherein the arch is formed on opposite sides of the exterior of the C-shaped band and slightly back from the edges of the opening, the arch further extending perpendicular over the C-shaped band; and
   an alignment tube guide projecting perpendicularly outward from the top of the arch and extending axially away from the femoral head, wherein an outer diameter of the alignment tube guide matches a width of the arch and further comprises a "snap off" feature at the top of the arch.

2. A femoral head surgical resurfacing aid according to claim 1, wherein the axis of the alignment tube guide is parallel and in-line with a planned femoral prosthesis implant axis.

3. A femoral head surgical resurfacing aid according to claim 1, further comprising:
   one or more stabilizers extending from the arch and configured to touch the femoral head when the C-shaped band is in a locked position.

4. A femoral head surgical resurfacing aid according to claim 1, wherein the aid is composed of a biocompatible, medical grade material.

5. A femoral head surgical resurfacing aid according to claim 4, wherein the biocompatible, medical grade material is selected from one of polycarbonate and acrylonitrile butadiene styrene.

6. A femoral head surgical resurfacing aid according to claim 1, wherein the aid is inscribed with at least one of patient information, prosthesis information, and rotation direction.

7. A femoral head surgical resurfacing aid according to claim 1, further comprising one or more registration points.

\* \* \* \* \*